United States Patent [19]
Salama

[11] Patent Number: 5,800,339
[45] Date of Patent: Sep. 1, 1998

[54] URINARY CONTROL VALVE

[75] Inventor: Fouad A. Salama, West Des Moines, Iowa

[73] Assignee: Opticon Medical Inc., West Des Moines, Iowa

[21] Appl. No.: 850,203

[22] Filed: May 2, 1997

Related U.S. Application Data

[60] Continuation-in-part of Ser. No. 725,030, Oct. 2, 1996, Pat. No. 5,693,001, which is a division of Ser. No. 233,308, Apr. 26, 1994, Pat. No. 5,634,877, which is a division of Ser. No. 61,770, May 14, 1993, Pat. No. 5,306,226, which is a division of Ser. No. 600,629, Oct. 22, 1990, abandoned, which is a continuation-in-part of Ser. No. 307,992, Feb. 9, 1989, Pat. No. 4,968,294.

[51] Int. Cl.⁶ ........................................................ A61F 2/02
[52] U.S. Cl. .................... 600/29; 604/247; 128/DIG. 25
[58] Field of Search ............................. 600/29, 30, 31; 604/247, 96; 128/DIG. 25

[56] References Cited

U.S. PATENT DOCUMENTS

| | | |
|---|---|---|
| 274,447 | 3/1883 | Kennish . |
| 1,923,501 | 8/1933 | Perry . |
| 1,972,895 | 9/1934 | Maccoy . |
| 3,320,972 | 5/1967 | High et al. . |
| 3,965,925 | 6/1976 | Gooch . |
| 4,143,853 | 3/1979 | Abramson . |
| 4,386,601 | 6/1983 | Trick . |
| 4,846,784 | 7/1989 | Haber . |
| 4,968,294 | 11/1990 | Salama ............................. 128/DIG. 25 |
| 5,009,391 | 4/1991 | Steigerwald . |
| 5,085,349 | 2/1992 | Fawcett . |
| 5,092,561 | 3/1992 | Moriuchi et al. . |
| 5,201,725 | 4/1993 | Kling . |
| 5,396,925 | 3/1995 | Poli . |
| 5,453,097 | 9/1995 | Paradis ............................... 604/247 |
| 5,601,207 | 2/1997 | Paczonay . |
| 5,707,356 | 1/1998 | Paul ................................... 604/247 |

Primary Examiner—Michael Powell Buiz
Assistant Examiner—Kevin Truong
Attorney, Agent, or Firm—Zarley, McKee, Thomte, Voorhees, & Sease

[57] ABSTRACT

A disc-like valve element in a control valve includes an outer peripheral ring to which leaf elements are integrally connected having a thickness which increases uniformly from the entire outer peripheral ring to the axial center forming a conical shaped valve element when in a closed condition. The side of the valve element facing the inlet end of the chamber is preferably flat functioning as a funnel to discharge urine when the valve element is moved to an open condition. The increased thickness at the axial center of the valve element is preferably the result of the side of the valve element facing the outlet end of the valve chamber increasing in thickness from the ring laterally inwardly and longitudinally outwardly to maximize flexibility of the leaf elements adjacent the ring and sealing at the axial center.

21 Claims, 4 Drawing Sheets

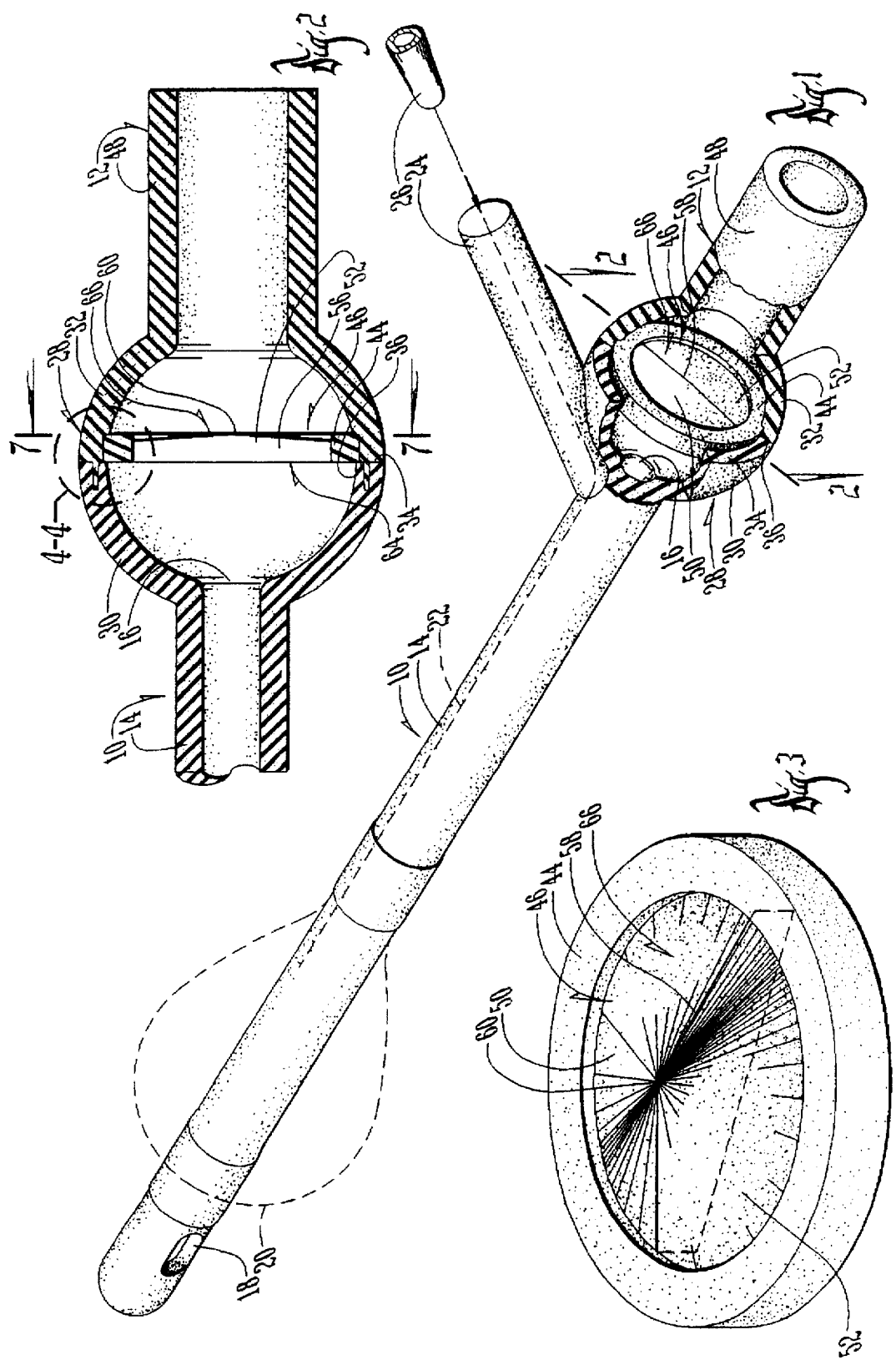

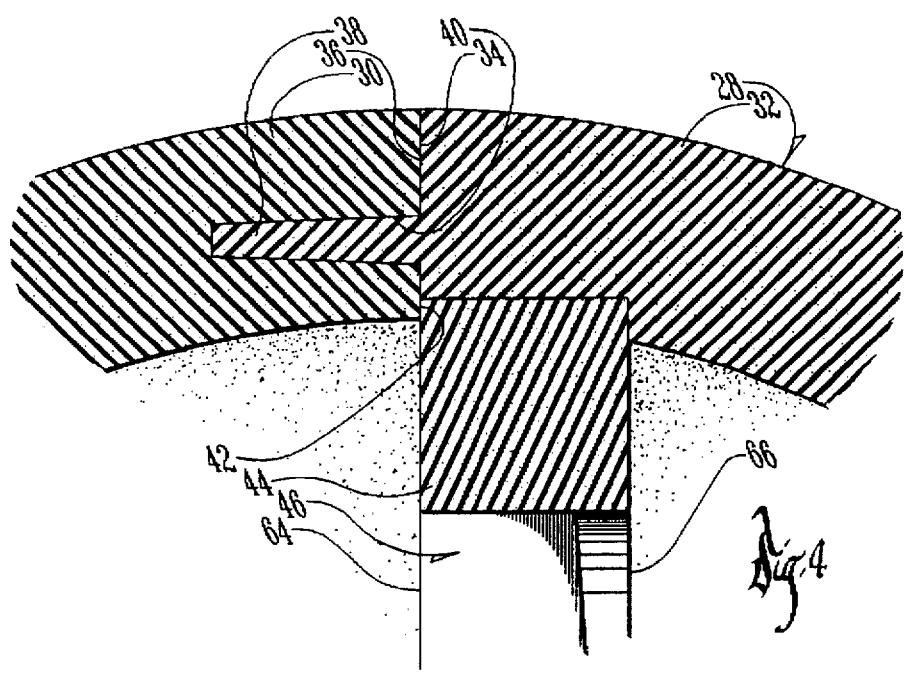
Fig. 4
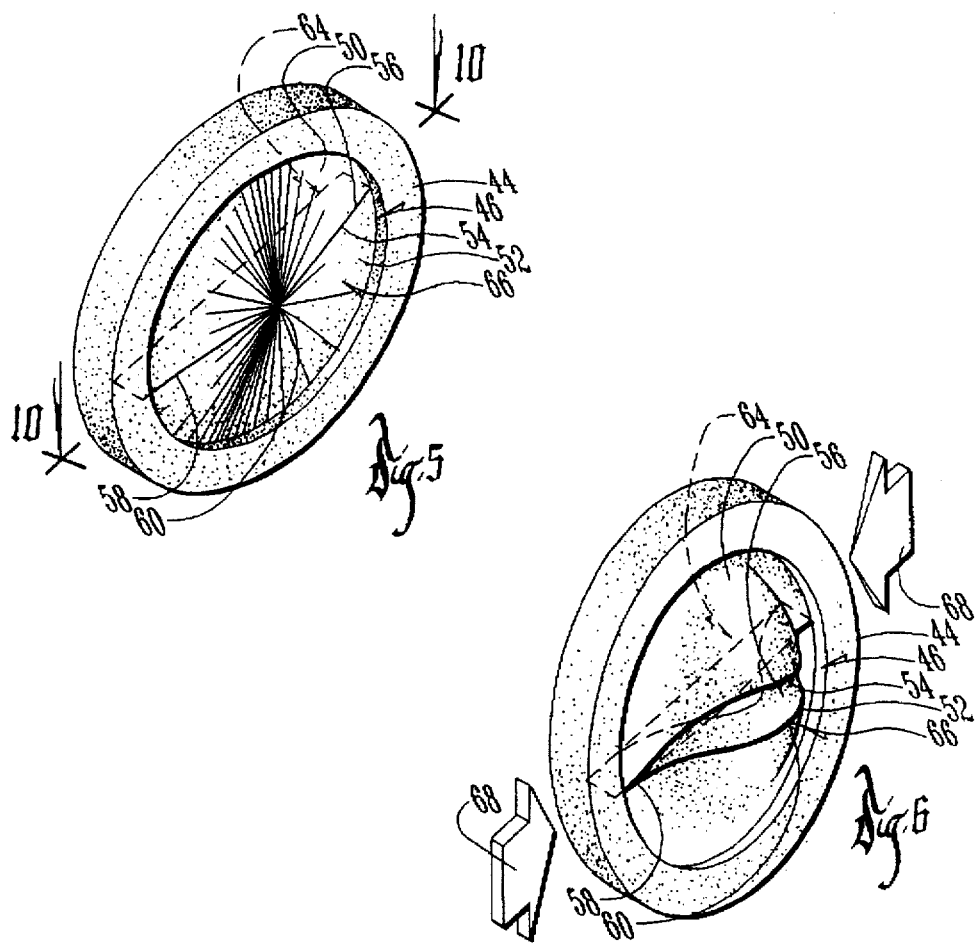
Fig. 5
Fig. 6

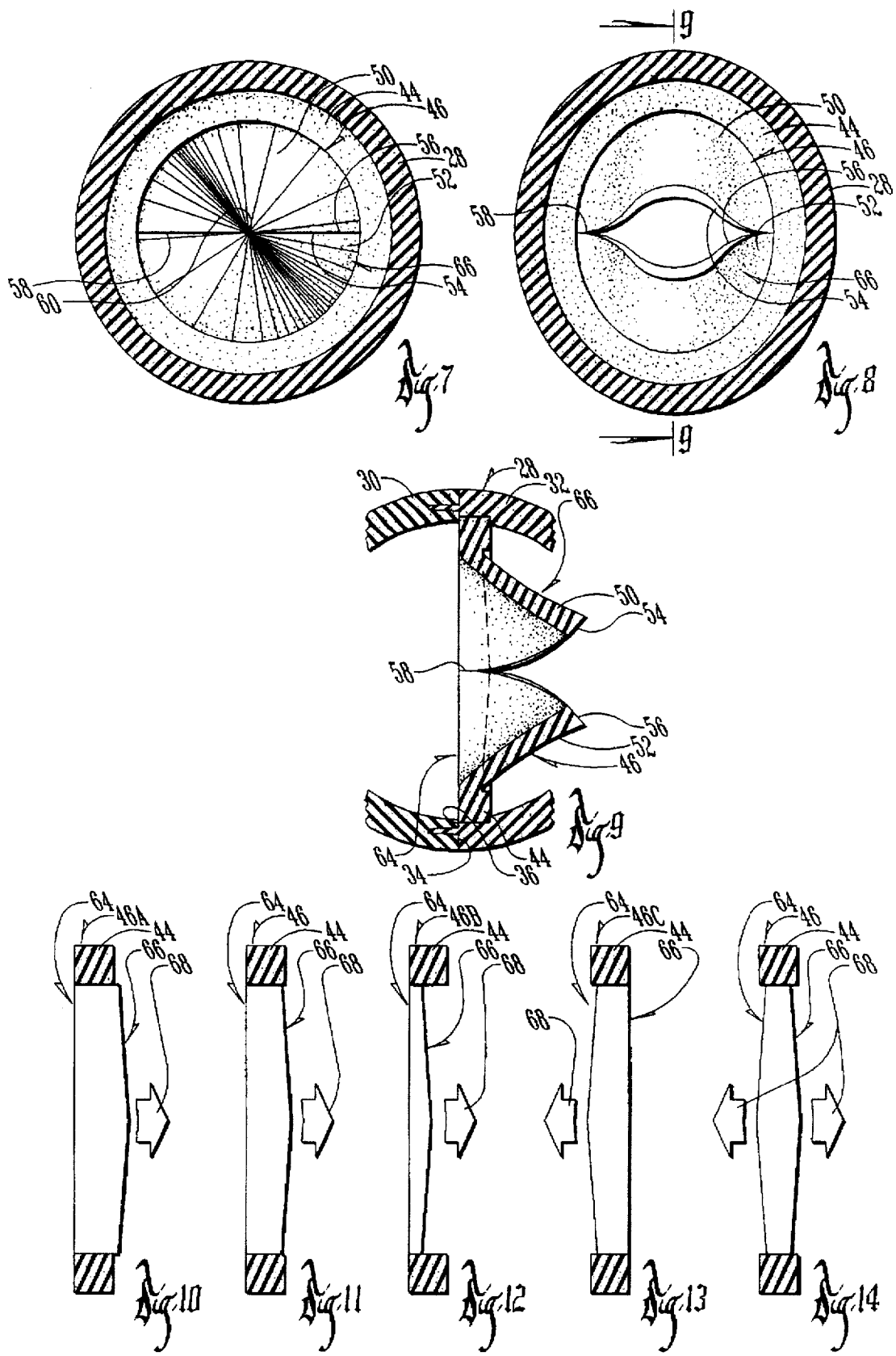

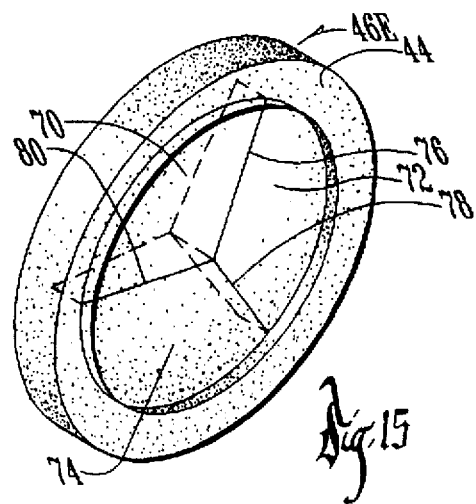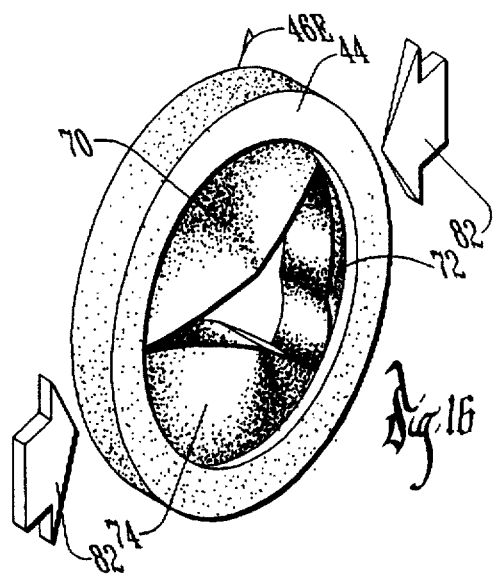

URINARY CONTROL VALVE

CROSS-REFERENCE TO RELATED APPLICATIONS

This is a continuation-in-part of application Ser. No. 08/725,030 filed Oct. 2, 1996 now U.S. Pat No. 5,695,001, URINARY CONTROL WITH INFLATABLE SEAL AND METHOD OF USING SAME, which is a divisional of Ser. No. 08/233,308 filed Apr. 26, 1994 now U.S. Pat. No. 5,634,877, which is a divisional of Ser. No. 08/061,770, filed May 14, 1993, U.S. Pat. No. 5,306,226, issued Apr. 26, 1994, which is a divisional of Ser. No. 07/600,629, filed Oct. 22, 1990, now abandoned, which is a continuation-in-part of Ser. No. 307,992, filed Feb. 9, 1989, U.S. Pat. No. 4,968,294, issued Nov. 6, 1990.

BACKGROUND OF THE INVENTION

This invention relates to a control valve for a urinary catheter. The valve replaces the bag commonly used with the catheter allowing discharge of urine by manual operation of the valve located outside the urethra.

The valve of this invention also is an improvement on my previous valve disclosed in U.S. Pat. No. 4,968,294, Nov. 6, 1990, and U.S. Pat. No. 5,306,226, Apr. 26, 1994. My prior valve included valve elements which extended laterally across the valve chamber but also towards the inlet end of the valve chamber. This valve performed very satisfactorily under normal conditions and best with higher urethra pressures. Slight leakage sometimes occurs at low pressures. The higher the pressure, the more pressure was applied to the valve elements to hold them in sealing engagement against each other in a closed position. Some urine would remain in the valve chamber between the valve elements and the chamber sidewall.

Thus, an improved urinary control valve is desired that will remain sealed and leak-proof under low pressure conditions and discharge all urine when the valve is opened.

SUMMARY OF THE INVENTION

The urinary control valve of this invention involves a valve body having a pair of half chamber sections which interface on opposite sides of a disc-like valve element. The valve element is of silicone material and includes a ring around the outer periphery to which a plurality of leaf elements are connected and extend inwardly towards an axial center. Thickness of the leaf elements increase uniformly from around the entire outer periphery towards the axial center to provide maximum flexibility adjacent the ring and maximum sealing between contiguous edges of the leaf elements at the axial center. Preferably, the increased thickness of the leaf elements at the axial center is result of the side elements facing the outlet of the chamber tapering laterally inwardly and longitudinally outwardly, thus, complementing the urine pressure on the opposite side of the leaf elements to cause them to open towards the chamber outlet. While a plurality of leaf elements may be used, two are preferred.

The ring of the disc-like valve element limits propagation of the slit formed between the leaf elements and provides for a stable mounting of the valve element on an annular shoulder formed in one half chamber wall with the outer peripheral edge of the other half chamber wall engaging the opposite side of the ring to limit ring movement. The outer edge of one chamber wall includes an annular rib which is received in an annular groove in the other chamber end edge and thus provides for positive sealing of the chamber wall at the interface of the two chamber half wall sections.

The disc-like valve element is opened by applying pressure to the valve body wall at opposite ends of the slit between the leaf elements. The two points where pressure should be applied are located by positioning an inflation tube on the outside of the chamber wall 90° from the opposite ends of the slit.

The side of the disc-like valve element facing the inlet end of the valve chamber is preferably flat thus allowing the valve leaf elements to function as a funnel when they begin to move to an open position towards the outlet end of the valve chamber thus assuring the valve chamber will be completely emptied when the valve is opened.

The thickness of the disc-like valve element at its axial center can vary from 0.031 inches to 0.095 inches with the thickness at the outer ring varying from 0.015 to 0.079. In each instance the increase is 0.016 inches. The preferred embodiment is 0.075 inches at the axial center and 0.059 at its outer periphery. The thickness of the peripheral ring is uniformly 0.062 inches.

BRIEF DESCRIPTION OF THE DRAWINGS

FIG. 1 is a fragmentary perspective view of the urinary control valve of this invention in a urinary balloon type catheter.

FIG. 2 is a cross-sectional view taken along line 2—2 in FIG. 1 of the valve body showing the disc-like valve element therein.

FIG. 3 is an enlarged perspective view of the valve element.

FIG. 4 is an enlarged fragmentary cross-sectional view of the interface of the valve body half chamber sections at their outer edges with each other and the ring of the valve element as indicated by the line 4—4 in FIG. 2.

FIG. 5 is an enlarged perspective view of the valve element in its closed condition while FIG. 6 is a similar view showing the valve element in an open condition.

FIG. 7 is a cross-sectional view taken along line 7—7 in FIG. 2 showing the valve element in its closed position.

FIG. 8 is a view similar to FIG. 7 but showing the valve element in an open condition.

FIG. 9 is a cross-sectional view taken along line 9—9 in FIG. 8 showing the valve element in an open condition.

FIGS. 10–14 are cross-sectional views taken along 10—10 in FIG. 5 illustrating valve elements with leaf elements of different thickness and the direction which the leaf elements move to an open position with FIG. 11 representing applicant's preferred embodiment.

FIG. 15 is a perspective view of an alternate embodiment valve element having three leaf elements in a closed position.

FIG. 16 is a view similar to FIG. 15 but showing the valve element in an open condition.

DESCRIPTION OF THE PREFERRED EMBODIMENT

The urinary control valve of this invention is generally referred to by the Reference 10 in FIG. 1 where it is shown as an integral part of a urinary catheter 12. The catheter 12 includes a tube 14 having a urine passageway 16 including an inlet 18 adapted to receive urine from the bladder. An inflatable balloon 20 is provided for seating and sealing the catheter in the bladder as described in my U.S. Pat. No.

5,306,226. An inflation passageway 22 extends along the length of the tube 14 and includes an inflation inlet portion 24 adapted to receive inflation liquid or gas from a pump device 26.

The tube 14 is connected to a valve body 28 which includes a pair of chamber half sections 30 and 32 having abutting outer peripheral edges 34 and 36 respectively. As seen in FIG. 4, the peripheral edge 36 includes an annular rib 38 received in a groove 40 formed in the annular edge 34 of the other chamber half section 30. The thickness of the peripheral edge 36 is reduced to form a shoulder 42 on which a ring 44 of the valve element 46 rests. The thickness of the edge 34 is sufficient to engage the ring 44 opposite the shoulder 42 to lock the ring in place and limit it against any movement.

The chamber half section 32 includes an outlet discharge tube portion 48.

The valve element 46 is disc-like in shape and includes a pair of leaf elements 50 and 52 which engage each other along contiguous inner edges 54 and 56 respectively. It is seen that the leaf elements 50 and 52 form a slit 58 which extends diametrically across the valve element. The valve elements 50 and 52 uniformly increase in thickness laterally inwardly and axially outwardly towards the axial center to form a conical shaped surface facing the outlet end 48 of the valve body 28. This construction provides maximum flexibility for the valve leaf elements 50 and 52 adjacent the ring 44 while providing maximum sealing action at the axial center 60 where movement towards an open position first occurs.

The ring 44 of the silicone valve element 46 limits propagation of the slit 58 which might otherwise occur through repeated opening and closing operations. The valve element 46 is opened by applying pressure as indicated by the arrows 62 at the diametrical opposite ends of the slit 58. These pressure points on the valve body are located by the user noting that the inflation tube portion 24 is positioned on the valve body 28 at a point 90° from either end of the diametrical slit 58. When pressure is applied to the ring 44 at opposite ends of the slit 58, the leaf elements 50 and 52 deflect axially outwardly in the direction of increased thickness and take on the shape as shown in FIGS. 6, 8 and 9. The leaves 50 and 52 are preferably flat on the inlet side 64 and are tapered on the outlet side 66 as seen in FIG. 10 thus allowing the fluid pressure on the inlet side 64 to combine with the natural tendency of the leaf elements to open in the direction of the taper on the outlet side. It is seen in FIG. 9 that the leaf elements 50 and 52 form a funnel opening toward the outlet 48 of the valve body 28 thus assuring the valve body 28 is completely emptied through each operation of the control valve 10.

The valve element 46 in FIG. 11 represents applicant's preferred embodiment and has an axial center of thickness of 0.075 inches with an outer thickness adjacent the ring 44 of 0.059 inches. The valve element 46A in FIG. 10 has an axial center thickness of 0.095 inches and an outer edge thickness of 0.079 inches. The valve element 46B of FIG. 12 has a center axial thickness of 0.031 inches and an outer leaf element thickness of 0.015 inches. In FIG. 13, the valve element 46C has an inner axial thickness of 0.062 inches and an outer leaf thickness of 0.046 inches. The ring 44 thickness is uniformly 0.062 inches.

The arrows 68 in FIGS. 10–14 indicate the direction of movement for the leaf elements. While it is preferred that the leaf elements open in the direction of the tapered surface, as seen in FIGS. 10–13, it is seen in the leaf element 46D in FIG. 14 that if a taper is provided on both surfaces, they can open in either direction. In FIG. 13, the arrow 68 indicates that while the leaf elements open in the direction of the taper, they also are opening against the fluid pressure in the valve chamber.

A further embodiment of the disc-like element is shown in FIGS. 15 and 16 and referred to by the Reference 46E and includes three leaf elements 70, 72 and 74 which engage each other along their contiguous inner edges to form slit portions 76, 78 and 80. With this embodiment, while it is preferred that pressure as indicated by the arrows 82 be applied at the end of the slits, pressure can be applied anywhere around the periphery of the ring 44 to cause the valve elements to move to an open position.

The silicone used in manufacturing the disc valve element 46 is manufactured by Bayer Silicone under the name Basilone LSR 4050 and is available through Quality Synthetic Rubber, Twinsburg, Ohio. The valve body chamber half sections 30 and 32 are also made from silicone material.

It is thus seen that a urinary control valve of simple construction has been provided which assures non-leak operation through a range of fluid pressures from normal to very low pressure. The pressure required to operate the valve is minimized while the sealing action between the valve leaf elements is maximized by the conical configuration which provides maximum thickness at the axial center and minimal thickness at their peripheral edges where flexing occurs during the opening and closing operation.

What is claimed is:

1. A urinary control valve comprising,
    a flexible valve body having inlet and outlet openings at opposite ends of a chamber,
    a valve means extending laterally across said chamber between said inlet and outlet openings and having an axial center, said valve means having an outer peripheral edge and including a plurality of flexible leaf sections in a common plane and having contiguous inner edges defining a slit, said contiguous inner edges sealingly engaging each other when said valve means is in a closed position and spaced apart when in an open position, said leaf sections increase in thickness uniformly from the entire outer peripheral edge toward said axial center and said valve means adapted to move to said open position in response to pressure on opposite sides of said valve body and return to said closed position in response to memory of said flexible leaf sections.

2. The urinary control valve of claim 1 wherein said plurality of flexible leaf sections are defined as two flexible leaf sections which have opposed contiguous inner edges which extend substantially across said chamber.

3. The urinary control valve of claim 2 wherein said valve body includes a urinary tube connected to said inlet opening, and an inflation tube is associated with said urinary tube and includes an inflatable balloon at one end and an inflation inlet opening means at its opposite end, said valve body having an outside wall surface and said opposite end having said inflation inlet opening means being positioned on the outside surface of said valve body at a point midway between the opposite ends of said slit in said valve element to provide a reference for locating said opposite ends of said slit for applying pressure to said valve body to open said valve means.

4. The urinary control valve of claim 1 wherein said plurality of flexible leaf sections are defined as three flexible leaf sections of equal size and shape, said valve means is adapted to move to said open position in response to pressure on opposite sides of said valve means and return to said closed position in response to memory of said flexible leaf sections.

5. The urinary control valve of claim 1 wherein said leaf sections have oppositely facing sides, and one of said sides is flat and the other side is tapered laterally inwardly and axially outwardly to provide said leaf means with increased thickness at its axial center.

6. The urinary control valve of claim 5 wherein said tapered other side faces said outlet end of said chamber.

7. The urinary control valve of claim 5 wherein the thickness of said leaf elements at said increased thickness axial center is between 0.031 inch and 0.095 inch.

8. The urinary control valve of claim 5 wherein a urinary tube is connected to said inlet opening of said valve body, and said urinary tube being adapted to be positioned in a urethra, said tapered one side of said leaf sections faces toward said outlet opening in said valve body whereby the direction of said taper and the urine pressure on said flat side will cause said leaf sections to open towards said outlet opening.

9. The urinary control valve of claim 1 wherein said leaf elements have oppositely facing sides which taper laterally inwardly and axially outwardly to provide said leaf means with increased thickness at its axial center.

10. The urinary control valve of claim 9 wherein the thickness of said leaf sections at said increased thickness axial center is between 0.031 inch and 0.095 inch.

11. The urinary control valve of claim 1 wherein said flexible leaf sections are positioned in and integral with a ring along its inner peripheral edge, said ring having an outer peripheral edge and opposite sides, and said chamber being defined by a chamber wall which is engaged by said ring outer peripheral edge.

12. The urinary control valve of claim 11 wherein said chamber is formed by a pair of half chamber sections and said valve means is positioned at the intersection of said half chamber sections.

13. The urinary control valve of claim 12 wherein an annular shoulder is provided in one of said half chamber sections and said valve means is positioned on said annular shoulder.

14. The urinary control valve of claim 13 wherein said half chamber sections include outer peripheral edges, said one half chamber section outer peripheral edge being reduced in thickness to form said annular shoulder, and said other outer peripheral edge having a thickness allowing it to engage the other side of said ring and said outer peripheral edge of said one chamber half section to limit movement of said valve means ring within said chamber.

15. The urinary control valve of claim 12 wherein an annular shoulder is provided in one of said half chamber sections and one side of said ring of said valve means is positioned on said annular shoulder.

16. The urinary control valve of claim 15 wherein said half chamber sections include outer peripheral edges, one of said outer peripheral edges includes an outwardly extending annular rib received in an annular groove in the outer peripheral edge of said other half chamber section.

17. The urinary control valve of claim 11 wherein said ring is thicker than the outer peripheral edge of said leaf sections whereby lateral outward propagation of said slit will be limited.

18. The urinary control valve of claim 1 wherein said increase in thickness of said leaf sections at said axial center is approximately 0.016 inch.

19. The urinary control valve of claim 1 wherein said outer periphery edge of said leaf sections is approximately 0.059 inches thick and said axial center is approximately 0.075 inches thick.

20. The urinary control valve of claim 1 wherein a urinary tube is connected to said inlet opening of said valve body, and said urinary tube being adapted to be positioned in a urethra.

21. The urinary control valve of claim 1 wherein said valve means is injection molded silicone material.

* * * * *